(12) United States Patent
Lambertus et al.

(10) Patent No.: US 8,613,215 B2
(45) Date of Patent: Dec. 24, 2013

(54) APPARATUS AND METHOD FOR MULTI-DIMENSIONAL GAS CHROMATOGRAPHY

(75) Inventors: Gordon Lambertus, Wellesley, MA (US); William Steinecker, Farmersville, OH (US)

(73) Assignees: Schlumberger Technology Corporation, Sugar Land, TX (US); 3M Innovative Properties Company, Saint Paul, MN (US)

( * ) Notice: Subject to any disclaimer, the term of this patent is extended or adjusted under 35 U.S.C. 154(b) by 606 days.

(21) Appl. No.: 12/636,858

(22) Filed: Dec. 14, 2009

(65) Prior Publication Data

US 2010/0154511 A1    Jun. 24, 2010

Related U.S. Application Data

(60) Provisional application No. 61/140,094, filed on Dec. 23, 2008.

(51) Int. Cl.
*G01N 30/46* (2006.01)

(52) U.S. Cl.
USPC .............................. 73/23.42; 95/86; 96/104

(58) Field of Classification Search
USPC .................. 73/23.42; 95/86; 96/104
See application file for complete search history.

(56) References Cited

U.S. PATENT DOCUMENTS

| | | | | |
|---|---|---|---|---|
| 4,016,074 A | * | 4/1977 | Porter | 210/659 |
| 4,962,662 A | * | 10/1990 | Berger | 73/23.42 |
| 5,049,509 A | * | 9/1991 | Szakasits et al. | 436/140 |
| 5,152,176 A | * | 10/1992 | Bryselbout et al. | 73/23.41 |
| 5,281,256 A | * | 1/1994 | Sacks et al. | 95/86 |
| 5,611,846 A | * | 3/1997 | Overton et al. | 96/102 |
| 6,575,015 B2 | * | 6/2003 | Lechner-Fish et al. | 73/23.42 |
| 6,776,025 B2 | * | 8/2004 | Lechner-Fish | 73/23.41 |
| 6,968,729 B1 | * | 11/2005 | Karlsson et al. | 73/23.41 |
| 7,241,424 B2 | * | 7/2007 | Guan et al. | 422/130 |
| 8,322,189 B2 | * | 12/2012 | Wang | 73/23.22 |
| 2002/0148353 A1 | | 10/2002 | Seeley | |
| 2007/0193336 A1 | * | 8/2007 | McCurry et al. | 73/23.42 |
| 2008/0092639 A1 | * | 4/2008 | Lee | 73/61.52 |

FOREIGN PATENT DOCUMENTS

| | | | |
|---|---|---|---|
| GB | 1257461 | * | 12/1971 |
| GB | 1291724 | * | 10/1972 |

* cited by examiner

*Primary Examiner* — Daniel S Larkin
(74) *Attorney, Agent, or Firm* — Daryl R. Wright; Tim Curington; Robin Nava

(57) ABSTRACT

A method and apparatus for two-dimensional gas chromatography (GC), including a valve having first and second positions (P1, and P2), and first through fourth sample flow paths (FP1-FP4). In P1, a first gas sample is collected from a first dimension GC column via FP1, a first pressure source and a first, second dimension GC column are connected via FP2, a second pressure source and a second, second dimension GC column are connected via FP3, and FP4 is disconnected. In P2, the first sample in FP1 is introduced to the second, second dimension GC column via FP1, with aid of the second pressure source, a second gas sample is collected from the first dimension GC column via FP2, the first pressure source and the first, second dimension GC column via FP4 are connected, and FP3 is disconnected.

19 Claims, 8 Drawing Sheets

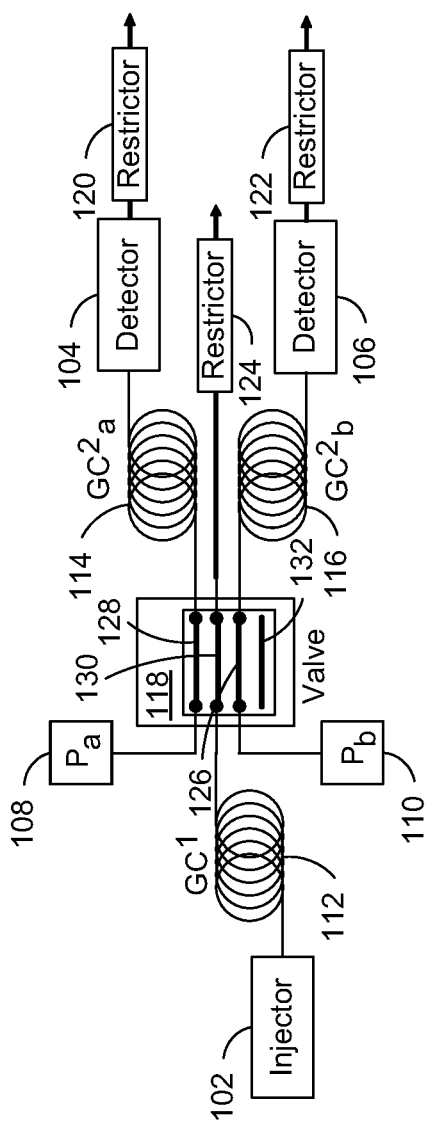

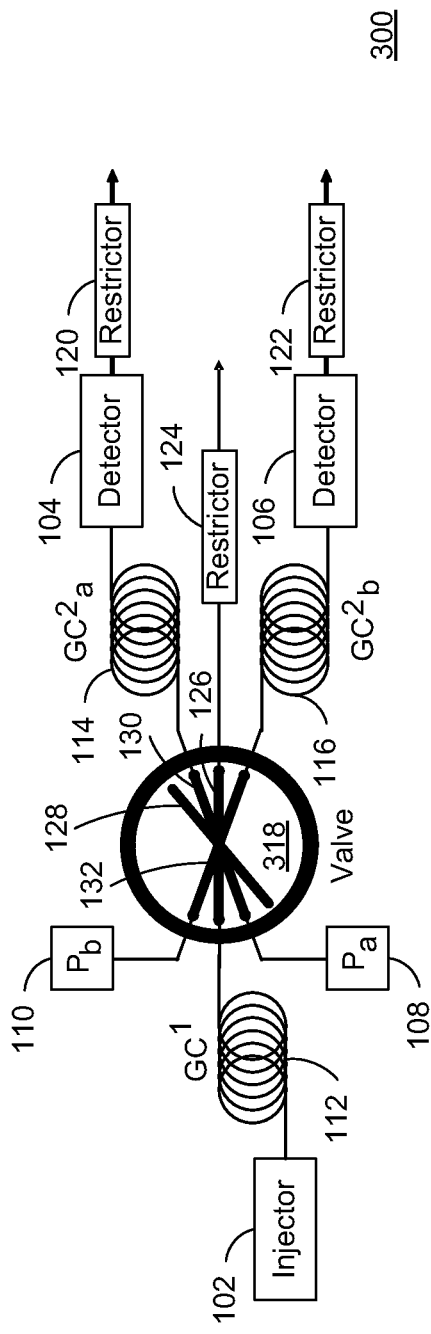
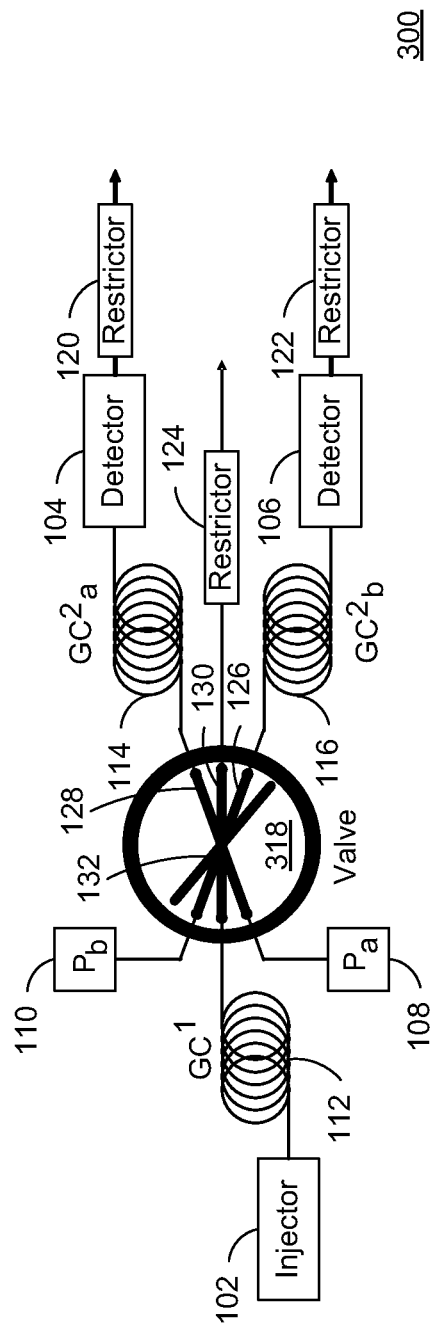
FIG. 3A
FIG. 3B

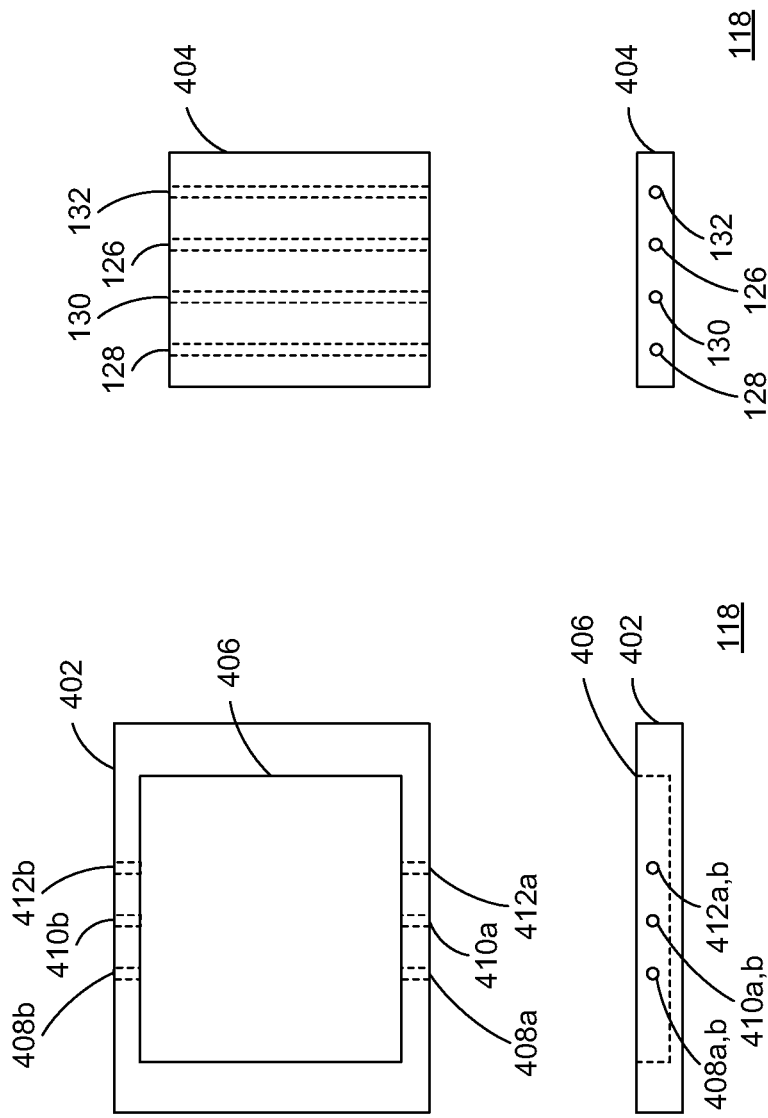

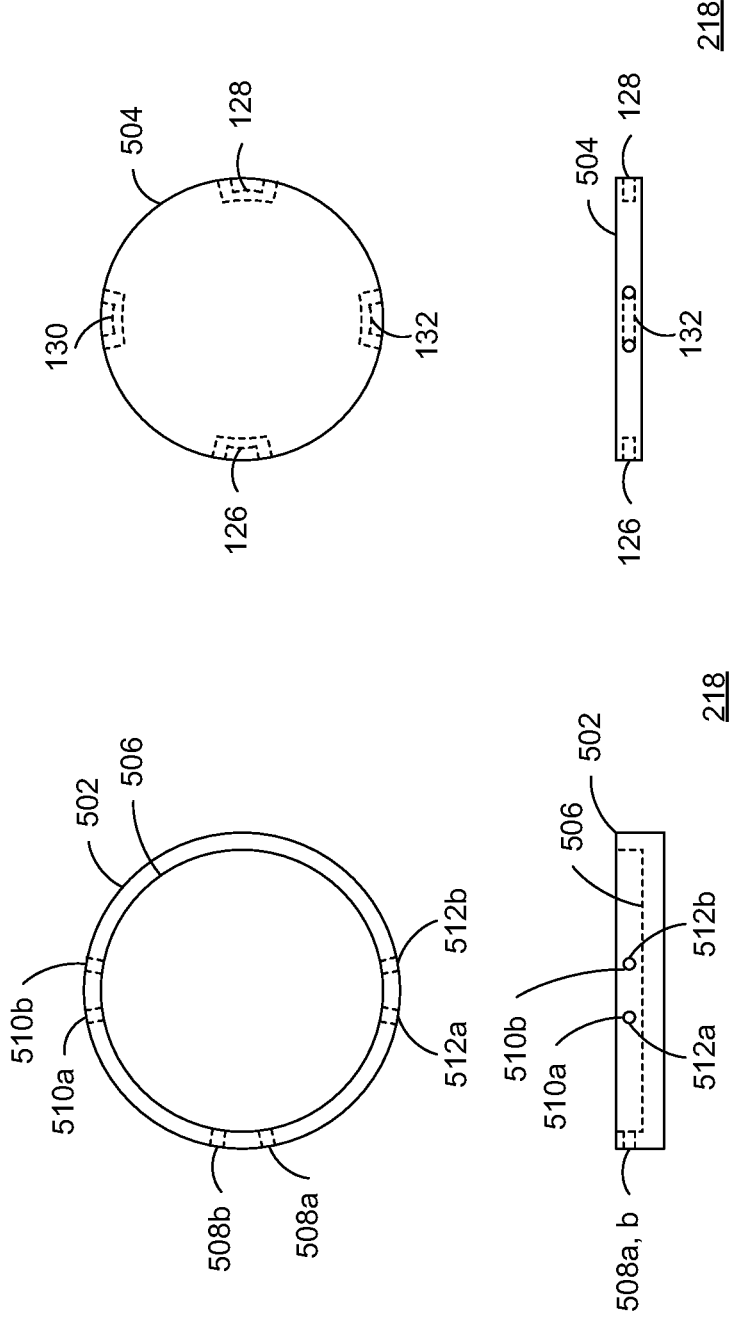

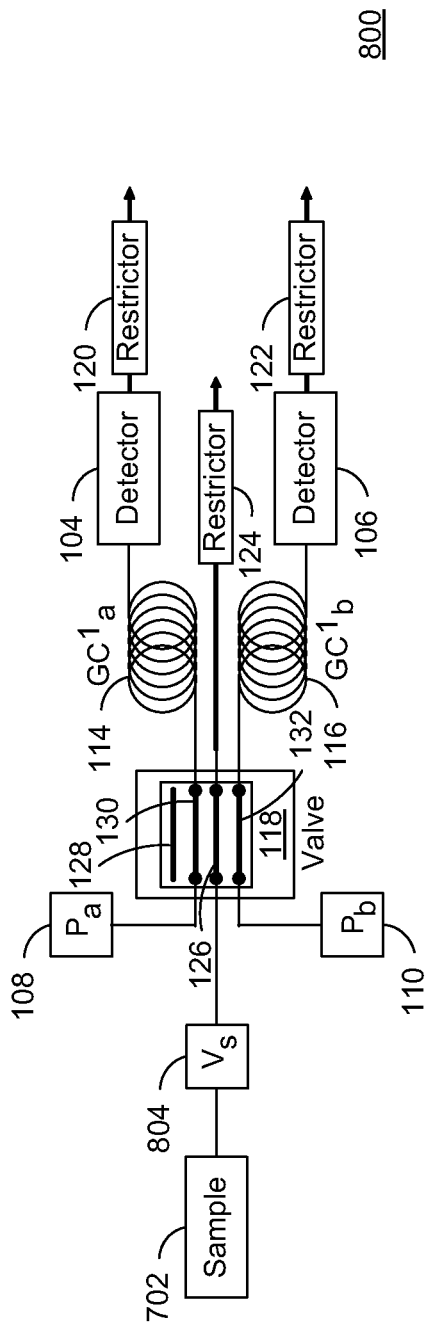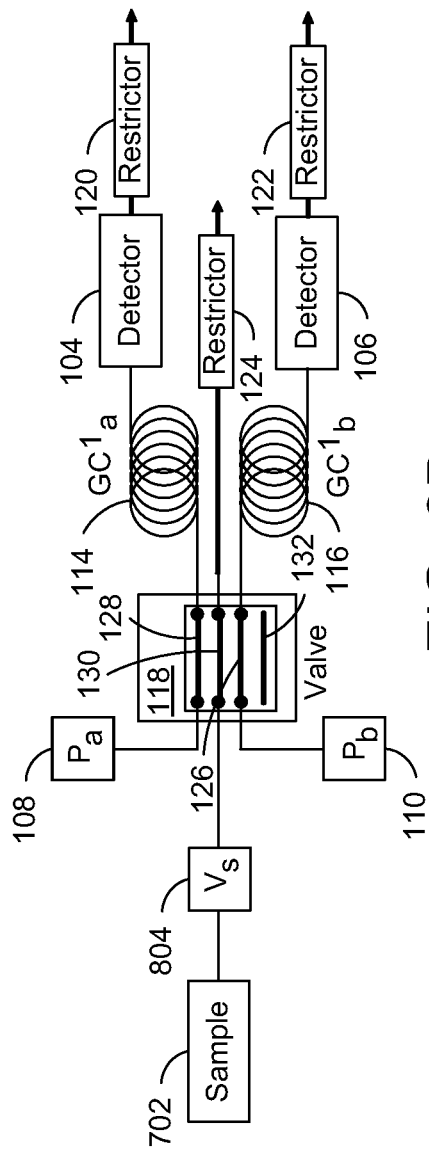

APPARATUS AND METHOD FOR MULTI-DIMENSIONAL GAS CHROMATOGRAPHY

CROSS-REFERENCE TO RELATED APPLICATION

The present application is based on and claims priority to U.S. Provisional Patent Application No. 61/140,094, filed Dec. 23, 2008.

TECHNICAL FIELD

The present invention generally relates to gas chromatography, and more particularly to valve based modulation for comprehensive two-dimensional gas chromatography.

STATE OF THE ART

Multi-dimensional gas chromatography is an advanced field where multiple gas-phase separations are performed in series on a single sample. A modulator is used to periodically collect and inject effluent from each separation column into a subsequent separation column. Typically, the modulator is actuated according to a constant schedule. It is necessary to tune the separation of each subsequent stage, such that an entire separation is completed within each cycle of the modulator. This sequence allows for independent determination of the retention time of each component on each dimension of the separation. Absent a modulation device, determination of the retention characteristics of each dimension is not easily isolated and may be superimposed. It is common practice in the art to use two stages, sometimes with multiple parallel separations in each dimension. The use of two stages is typically referred to as comprehensive two-dimensional gas chromatography (abbreviated herein as GCXGC, GC-GC, or 2DGC).

The term comprehensive is applied to methods where the entire injected sample is analyzed in the system. Although, in some cases, systems that analyze less than 100% of the sample are still considered comprehensive, for example, if the modulation frequency is high-enough that a reasonable time resolution of the first dimension separation is still achieved, as described in United States Patent Application Publication No. 20020148353 A1 of Seeley. GCXGC methods that rely on two parallel columns in the second dimension have been referred to as GCX2GC. However, these methods are clearly a sub-class of GCXGC, and therefore the term GCXGC will be predominately used herein.

The modulator in a GCXGC instrument is highly recommended. Only by capturing the effluent from the first dimension column and reintroducing it as an injection to the second dimension column(s), can the retention times of both columns be known simultaneously, while still producing a two-dimensional separation.

The modulation frequency is the frequency at which the collected sample is injected into the second dimension column. Typically, this is on the order of 1 cycle per 1-10 seconds (e.g., 0.10-1.0 Hz). In common practice, the modulation frequency is determined by the time scale of the second dimension separation (e.g., typically 1-10 seconds). Based on this value, the time scale of the first dimension separation is then designed, such that each eluting peak will be modulated into several or more injections to the second dimension. However, with most modulators the flow from the first and second dimension columns are related, and therefore independently optimizing the flow conditions of the first and second dimensions is difficult. A modulator that isolates the first and second dimension column flow rates provides a significant advantage in allowing independent flow optimization for both separations. The isolation of flows also allows for much faster separations, as many high speed GC configurations require much faster flow rates than are typically used for first dimension separations.

Generally, the first dimension separation is intentionally designed to produce wider eluting bands (and e.g., longer separation times) in order to be compatible with slower modulation frequencies and longer second dimension separations.

An advantage of GCXGC is the order of magnitude improvement in peak capacity over single-dimension separations. Single dimension systems with multiple columns offer similar avenues of selectivity. However, they do not offer the peak capacity of GCXGC. Another advantage to GCXGC, with certain modulators, is improved signal to noise ratios and therefore lower system levels of detection, but this may be heavily dependent on the type of modulator and the nature of the second dimension separation.

Modulators for GCXGC can be grouped into two categories, thermal modulators and valve modulators, wherein thermal modulators function through temperature cycling of a segment of column, bare tubing, or adsorbent/absorbent filled tubing. The sample is captured and periodically thermally desorbed into the second stage (e.g., the modulator is repeatedly heated and cooled). The main advantage with thermal modulators is a significant increase in analyte concentration (and e.g., proportional decrease in system limits of detection) via the preconcentration provided by the trapping of sample in the "cold" regions of the modulator. However, typical thermal modulators require that the carrier gas flow from the first dimension also be used for the second dimension, which can make it difficult to optimize flow conditions for both separation stages. Another advantage to thermal modulators is that, due to rapid heating cycles, they are capable of generating very sharp injection pulses that permit faster and higher resolution separations in the second dimension. The resolution of the second dimension is the major contributor to the total peak capacity of the whole GCXGC system. A potential disadvantage to thermal modulators is the vapor pressure range limitation of most thermal cycling systems. For example, for virtually all types of adsorbent materials or trapping temperatures some vapors will be too volatile to adsorb/absorb and some will be too low in volatility to be easily desorbed, for a given temperature range.

Valve modulators can act to divert flow between multiple flow paths to achieve pulses of effluent entering the first column, for example, as described in United States Patent Application Publication No. 20020148353 A1 of Seeley. Commonly, vents are used at one or more connections, which is a potential source of sample loss (and therefore a non-comprehensive GCXGC separation), and dilution is often a side-effect of the flow manipulation process. Often, a two-position three-way valve or a sampling valve is used to collect the sample and reintroduce it into the second dimension column. Common examples of these valves are rotary valves with sampling loops or sampling grooves on the rotor, face-sealing valves with rotary or sliding plates, and diaphragm valves with sample grooves or external sampling loops.

Valve modulators have the advantage of avoiding the engineering issues of repetitive modulator heating and cooling, and therefore are more durable, easier to manufacture, and usually capable of much faster modulation frequencies. Valve modulators also have the advantage of not being limited to specific analyte vapor pressure ranges, as is the case with thermal modulators. In some cases, an additional advantage arises in the isolation of carrier gas flows, which results in easier flow optimization. However, the significant disadvantage to valve modulators is that little or no increase in sample concentration is achieved and the injection pulses are therefore generally wider than for thermal modulators.

SUMMARY OF THE INVENTION

Therefore, there is a need for a method and apparatus (which also may be referred to herein as a "system") that addresses the above and other problems. The above and other needs and problems are addressed by the exemplary embodiments of the present invention, which provide a method and apparatus, including a valve based modulation technique for two-dimensional gas chromatography (e.g., GCXGC, GC-GC, or 2DGC) and which has several advantages. In combination with dual high-pressure detectors, significant improvements in system performance are possible. A traditional first dimension GC separation is performed and the effluent exits into a sampling valve. The valve is designed such that it has two positions, both of which allow for collection of an effluent sample and injection of a previously collected sample. The valve is cycled between the two positions, such that collected samples are introduced into each of two secondary columns in an alternating fashion. Advantageously, this allows for a two-fold increase in the modulation frequency, without a reduction in the separation time of either of the second stage separations (or conversely, a 2-fold increase in separation time in the second dimension with no reduction in modulation frequency). In addition, the valve provides flow isolation between all three columns, allowing for true optimization of all columns' flow rates. By pressurizing each of the second stage separations (e.g., via a restrictor or any suitable back-pressure regulator on each of the respective outlets of the detectors), the sample can be compressed during the introduction to each of the second stages, resulting in a significant increase in analyte concentration, which will significantly improve limits of detection. A reduced modulator injection band width has significant implications for the second dimension separation. For example, faster and/or higher resolution separations become possible and total peak capacity is increased. Compression ratios of 100:1 or more are easily achievable.

Accordingly, in exemplary aspects of the present invention there is provided an apparatus for two-dimensional gas chromatography, comprising: a valve including first and second positions, and first, second, third, and fourth flow paths, wherein the valve, while in the first position, is configured to: collect a first gas sample from a first dimension gas chromatography column via the first flow path, provide a connection between a first pressure source and a first, second dimension gas chromatography column via the second flow path, provide a connection between a second pressure source and a second, second dimension gas chromatography column via the third flow path, and maintain the fourth flow path in a disconnected state; and the valve, while in the second position, is configured to: introduce the first collected gas sample in the first flow path to the second, second dimension gas chromatography column via the first flow path, with aid of the second pressure source, collect a second gas sample from the first dimension gas chromatography column via the second flow path, provide a connection between the first pressure source and the first, second dimension gas chromatography column via the fourth flow path, and maintain the third flow path in a disconnected state. The valve may be a sliding-plate type valve, or a rotary type valve.

The apparatus for two-dimensional gas chromatography may be further described wherein a time to collect the first gas sample before moving the valve to the second position is equal to or less than a volume of the first gas sample divided by a volumetric flow rate of an outlet of the first dimension gas chromatography column. In addition, the time spent by the valve in the second position may be equal to the time to collect the first gas sample. A separation time may be employed on both the first and second, second dimension gas chromatography columns, which may be less than a total time spent in the first and second valve positions, and which may be equal to twice a reciprocal of a modulation frequency.

The apparatus may further comprise an injector coupled to an inlet of the first dimension gas chromatography column for injecting a gas to be analyzed into the first dimension gas chromatography column. Such apparatus may further comprise a first restrictor coupled to the valve for restricting the gas injected into the first dimension gas chromatography column by the injector to increase a compression ratio in the first dimension gas chromatography column.

The apparatus for two-dimensional gas chromatography may also comprise a first detector coupled to an outlet of the first, second dimension gas chromatography column for performing gas chromatography detection in the first, second dimension gas chromatography column. Such apparatus may further comprise a second restrictor coupled to the first detector for restricting gas in the first, second dimension gas chromatography column to increase a compression ratio in the first, second dimension gas chromatography column. It should be noted however, that the first detector may comprise a thermal conductivity detector (TCD).

The apparatus for two-dimensional gas chromatography may also comprise a second detector coupled to an outlet of the second, second dimension gas chromatography column for performing gas chromatography detection in the second, second dimension gas chromatography column. Such apparatus may further comprise a third restrictor coupled to the second detector for restricting gas in the second, second dimension gas chromatography column to increase a compression ratio in the second, second dimension gas chromatography column. It should be noted however, that the second detector may comprise a thermal conductivity detector (TCD).

In another aspect of the present invention there is provided a method for comprehensive two-dimensional gas chromatography conducted with a valve having first and second positions, and first, second, third, and fourth flow paths, the method comprising: putting the valve in the first position, and: collecting a first gas sample from a first dimension gas chromatography column via the first flow path, providing a connection between a first pressure source and a first, second dimension gas chromatography column via the second flow path, providing a connection between a second pressure source and a second, second dimension gas chromatography column via the third flow path, and maintaining the fourth flow path in a disconnected state; putting the valve in the second position, and: introducing the first collected gas sample in the first flow path to the second, second dimension gas chromatography column via the first flow path, with aid of the second pressure source, collecting a second gas sample from the first dimension gas chromatography column via the second flow path, providing a connection between the first pressure source and the first, second dimension gas chromatography column via the fourth flow path, and maintaining the third flow path in a disconnected state. Furthermore, the valve may be a sliding-plate type valve, or a rotary type valve.

The method for comprehensive two-dimensional gas chromatography may be further described wherein setting a time to collect the first gas sample before moving the valve to the second position may be equal to or less than a volume of the first gas sample divided by a volumetric flow rate of an outlet of the first dimension gas chromatography column. In addition, setting a time spent by the valve in the second position may be equal to the time to collect the first gas sample. Setting a separation time may be employed on both the first and second, second dimension gas chromatography columns to less than a total time spent in the first and second valve positions, and equal to twice a reciprocal of a modulation frequency.

The method may further comprise the step of injecting a gas to be analyzed into the first dimension gas chromatography column via an injector coupled to an inlet of the first dimension gas chromatography column. Such method may include restricting the gas injected into the first dimension gas chromatography column by the injector to increase a compression ratio in the first dimension gas chromatography column via a first restrictor coupled to the valve.

The method for comprehensive two-dimensional gas chromatography may further comprise the step of performing gas chromatography detection in the first, second dimension gas chromatography column via a first detector coupled to an outlet of the first, second dimension gas chromatography column. Such method may include restricting gas in the first, second dimension gas chromatography column to increase a compression ratio in the first, second dimension gas chromatography column via a second restrictor coupled to the first detector. The first detector may be a thermal conductivity detector (TCD).

The method may further comprise the step of performing gas chromatography detection in the second, second dimension gas chromatography column via a second detector coupled to an outlet of the second, second dimension gas chromatography column. Such method may include restricting gas in the second, second dimension gas chromatography column to increase a compression ratio in the second, second dimension gas chromatography column via a third restrictor coupled to the second detector. The second detector may comprise a thermal conductivity detector (TCD).

In a further aspect of the present invention there is provided an apparatus for gas chromatography, comprising: a valve including first and second positions, and first, second, third, and fourth flow paths, wherein the valve, while in the first position, is configured to: collect a first sample from a sample source via the first flow path, provide a connection between a first pressure source and a first gas chromatography column via the second flow path, provide a connection between a second pressure source and a second gas chromatography column via the third flow path, and maintain the fourth flow path in a disconnected state; and the valve, while in the second position, is configured to: introduce the first collected sample in the first flow path to the second gas chromatography column via the first flow path, with aid of the second pressure source, collect a second sample from the sample source via the second flow path, provide a connection between the first pressure source and the first gas chromatography column via the fourth flow path, and maintain the third flow path in a disconnected state. The first and second samples may be in a gas phase, or in a liquid phase. However, where the first and second samples are in a liquid phase, the apparatus may comprise a chamber provided between the sample source and the valve, wherein the chamber is configured to convert the first and second samples in the liquid phase to a gas phase.

In another aspect of the invention there is provided a method for gas chromatography conducted with a valve having first and second positions, and first, second, third, and fourth flow paths, the method comprising the steps of: putting the valve in the first position, and: collecting a first sample from a sample source via the first flow path, providing a connection between a first pressure source and a first gas chromatography column via the second flow path, providing a connection between a second pressure source and a second gas chromatography column via the third flow path, and maintaining the fourth flow path in a disconnected state; putting the valve in the second position, and: introducing the first collected sample in the first flow path to the second gas chromatography column via the first flow path, with aid of the second pressure source, collecting a second sample from the sample source via the second flow path, providing a connection between the first pressure source and the first gas chromatography column via the fourth flow path, and maintaining the third flow path in a disconnected state. The first and second samples may be in a gas phase, or in a liquid phase. However, where the first and second samples are in a liquid phase, the method may further comprise converting the first and second samples in the liquid phase to a gas phase via a chamber provided between the sample source and the valve.

Still other aspects, features, and advantages of the present invention are readily apparent from the entire description thereof, including the figures, which illustrates a number of exemplary embodiments and implementations. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIGS. 1A-1B illustrate an exemplary sliding-plate valve configuration;

FIGS. 3A-3B illustrate another exemplary rotary valve configuration;

FIGS. 4A-4B illustrate top and side views of the exemplary sliding-plate valve configuration of FIGS. 1A-1B;

FIGS. 5A-5B illustrate top and side views of the exemplary rotary valve configuration of FIGS. 2A-2B;

FIGS. 8A-8B illustrate a still further exemplary sliding-plate valve configuration.

DETAILED DESCRIPTION

Figure 2A:
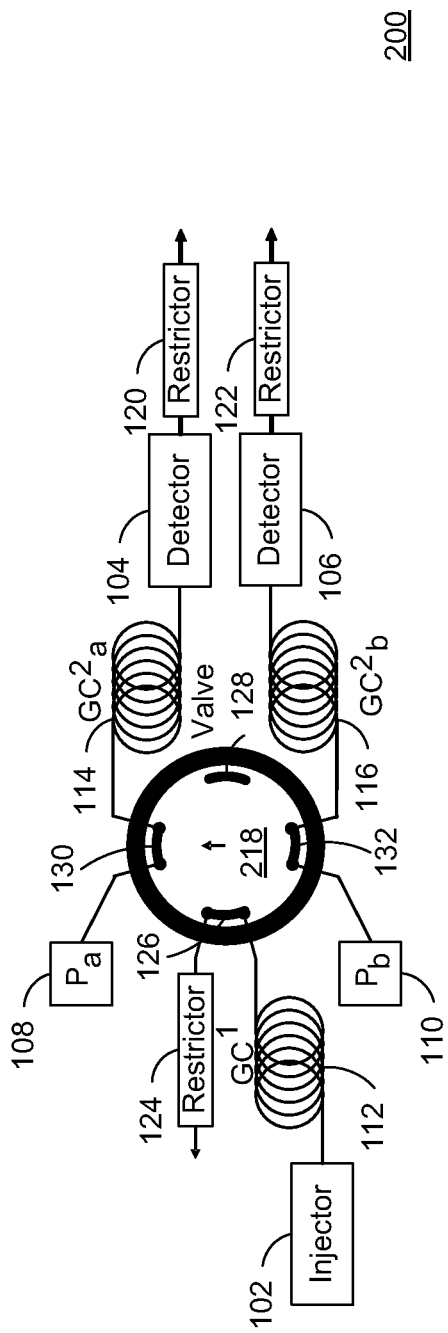
FIGS. 2A-2B illustrate an exemplary rotary valve configuration.

Various embodiments and aspects of the invention will now be described in detail with reference to the accompanying figures. The terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Referring now to the drawings, wherein like reference numerals designate identical or corresponding parts throughout the several views, and more particularly to FIGS. 1-3 thereof, there are illustrated exemplary valve based modulation systems 100-300 that can be used for two-dimensional gas chromatography (GC) (GCXGC, GC-GC, or 2DGC). In FIGS. 1-3, the respective exemplary valve modulation systems 100-300 for two-dimensional gas chromatography include injectors 102, detectors 104 and 106, pressure sources 108 and 110 ($P_a$ and $P_b$, respectively), GC columns 112, 114, and 116 ($GC^1$, $GC^2_a$, and $GC^2_b$, respectively), respective valves 118, 218 or 318, and restrictors 120, 122 and 124 (or e.g., any suitable back-pressure regulators). The GC columns 112, may also be referred to herein as "first dimension GC separator column," or "first dimension column," and each of the columns 114 and 116 may be referred to herein as "second dimension GC separator column," or "second dimension column."

Figure 2B:
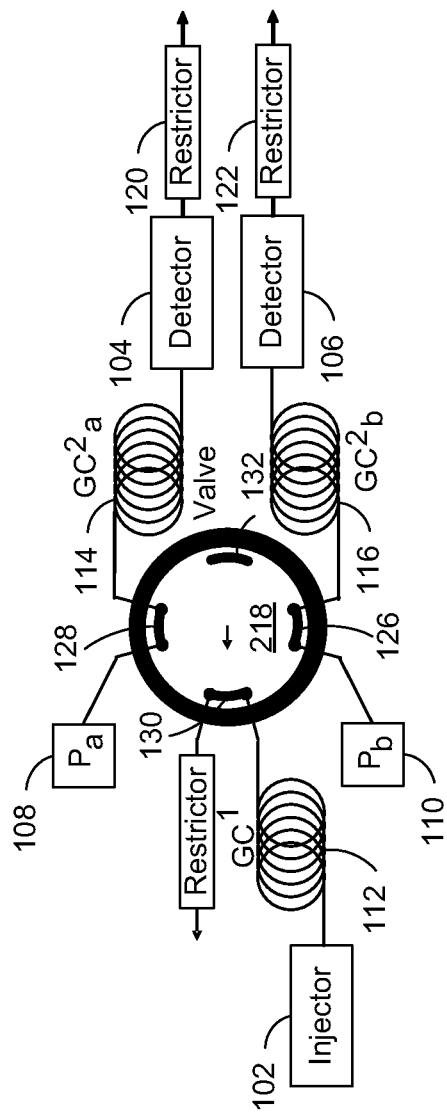

Each of the FIGS. 1-3 depicts a similar system, with the exception of the type of valve 118 (e.g., a sliding-plate type valve), 218 (e.g., a rotary type valve), and 318 (e.g., another rotary type valve) that is employed as the modulator. In each case, the respective valve 118, 218 or 318 is periodically cycled between positions 1 and 2, as illustrated in FIGS. 1A, 2A and 3A (position 1), and FIGS. 1B, 2B and 3B (position 2), respectively, to achieve modulation. The three types of exemplary valves 118, 218 and 318 are similar in ultimate function, but differ slightly in subtle details associated with the type of actuation and the nature of the sample flow paths within the moving portions of the valves 118, 218 and 318.

In each case, as shown in FIGS. 1-3, four sample flow paths (or "flow paths") exist within the movable portion of the valves 118, 218 and 318. These flow paths provide fluidic connections between three pairs of inlet/outlet flow paths at each of the two valve positions. One of these four flow paths is always disconnected in each position, as shown in FIGS. 1-3. The internal volume, length, and cross-section of each flow path are identical and equal to the sampling volume of the valve. Ideally, the cross-sectional area of each flow path is the same as that of each of the GC columns 112, 114, and 116. In the case that this is not possible (e.g. a megabore column is used in the first dimension column 112 and microbore columns are used for each second dimension columns 114 and 116), then the cross-sectional area should match the second dimension columns 114, and 116 to avoid extra-column band broadening on the faster separation (e.g., which likely has much less on-column band broadening). Alternatively, a tapered flow channel can be employed, which matches the first column 112 cross-section and the cross-section of the second columns 114 and 116. In all cases, the sampling volume should be chosen to match the injection volume required for the second stages (e.g., after accounting for the expected sample compression).

The term modulation frequency can create some ambiguity, as the frequency of the actuation of the valves 118, 218 and 318 is twice that of the frequency of injection into each second stage column (i.e., second dimension column). In the context of the present invention, the modulation frequency refers to the actuation frequency, or twice the injection frequency into each of the second dimension columns 114 and 116, although the injection to $GC^2_a$ (column 114) is offset from the injection to $GC^2_b$ (column 116) by one actuation.

In position 1, as shown in FIGS. 1A, 2A, and 3A, the effluent from $GC^1$ (column 112) is collected in the sample path 126 of the modulator valve, while other paths provide fluidic connections between $P_a$ (pressure source 108) and $GC^2_a$ (column 114), path 130, and $P_b$ (pressure source 110) and $GC^2_b$ (column 116), path 132, respectively. The flow path 128 indicates the disconnected flow path. After the sampling flow path 126 has been adequately filled (for comprehensive GCXGC, this is a time equal to or less than the sample volume divided by the $GC^1$ (column 112) outlet volumetric flow rate), the valve 118, 218 or 318 is actuated to position 2, as shown in FIG. 1B, 2B or 3B. This shifts the collected sample to the sample path 126 and introduces the collected sample to $GC^2_b$ (column 116) via the pressure source 110 ($P_b$), while effluent from $GC^1$ (column 112) is now collected on a different valve flow path 130. It is important to notice that the sample path 132 that was previously connecting $P_b$ (pressure source 110) to $GC^2_b$ (column 116) in FIGS. 1A, 2A, and 3A is now disconnected, and the previously disconnected sample path 128 is now providing flow between $P_a$ (pressure source 108) and $GC^2_a$ (column 114). After the sample volume has been adequately filled, the valve 118, 218 or 318 is cycled back to position 1 shown in FIGS. 1A, 2A, and 3A to introduce the collected sample into $GC^2_a$ (column 114) via the pressure source 108 ($P_a$) and sample path 130 and to collect another sample for $GC^2_b$ (column 116) in the sample path 126. Typically, the valve 118, 218 or 318 actuation frequency should be constant throughout each analysis and the time spent in position 1 and 2 will be equal. In an exemplary embodiment, the separation time employed on both $GC^2_a$ (column 114) and $GC^2_b$ (column 116) should be less than the total time period for position 1 and position 2, which is equal to twice the reciprocal of the modulation frequency.

By restricting the detector 104 and 106 outlets via the respective restrictors 120 and 122, the inlet pressure of the second dimension columns 114 and 116 ($GC^2_a$ and $GC^2_b$, respectively) can be elevated substantially. When the valve 118, 218 or 318 is actuated, the sample volume is compressed, which elevates analyte concentrations and reduces the injection band width proportionally. This generates significantly larger detector 104 and 106 signal-to-noise ratios (e.g., decreasing system limits of detection) for the same analyte sample. Compression ratios of 100:1 are easily achieved. In an exemplary embodiment, the detectors 104 and 106 are configured so as to be (1) capable of operating at this elevated pressure, and (2) have an outlet flow that can reasonably be restricted (e.g., a flame ionization detector with excessive exhaust gases would not be ideal). For example, a thermal conductivity detector (TCD), and the like, can be employed for the detectors 104 and 106. Advantageously, the TCD response time can be enhanced, because of the decreased mean free path of the carrier gas, as a result of the pressure elevation. However, in further exemplary embodiments, any other suitable detector can be employed, as will be appreciated by those skilled in the relevant art(s).

A compression ratio of 100:1 is large compared to the "preconcentration" factors typically observed with thermal modulators. Similar values could be obtained with very slow modulation frequencies with thermal modulators, but the cost of a decreased modulation frequency would be a substantially longer experiment time and/or decreased first-dimension time resolution. With the exemplary embodiments, however, signal-to-noise ratio enhancement is possible, while still maintaining or even increasing the modulation frequency (e.g., minimizing the time scale of the second dimension separation).

In FIG. 1, a sliding-plate valve 118 is employed, as detailed in FIGS. 4A-4B, showing top and side views of the valve 118. Advantageously, this type of modulator with this type of valve can work well with microfluidic systems. In FIGS. 4A-4B, the valve 118 includes valve body 402 with slide opening 406 for a sliding-plate 404. Advantageously, the entry ports 408a-412a and exit ports 408b-412b of the body 402, the sample paths 126-132 of the sliding-plate 404, and the like, can be microfabricated structures.

Similarly, FIGS. 5A-5B show top and side views of the valve 218 of FIG. 2. In FIGS. 5A-5B, the valve 218 includes circular valve body 502 with rotor opening 506 for a rotor 504, entry ports 508a-512a and exit ports 508b-512b of the circular valve body 502, and the sample paths 126-132 of the rotor 504. The rotating valve 218 can generally be created with a series of grooves for sample paths 126-132 used in a cylindrical or conical rotor 504. In the rotating valve 218, the sample grooves 126-132 pass multiple ports 508-512 during the actuation cycle, before settling in the final position. Advantageously, the entry ports 508a-512a and exit ports 508b-512b of the body 502, the sample paths 126-132 of the rotor 504, and the like, can be microfabricated structures.

Figures 6A, 6B:
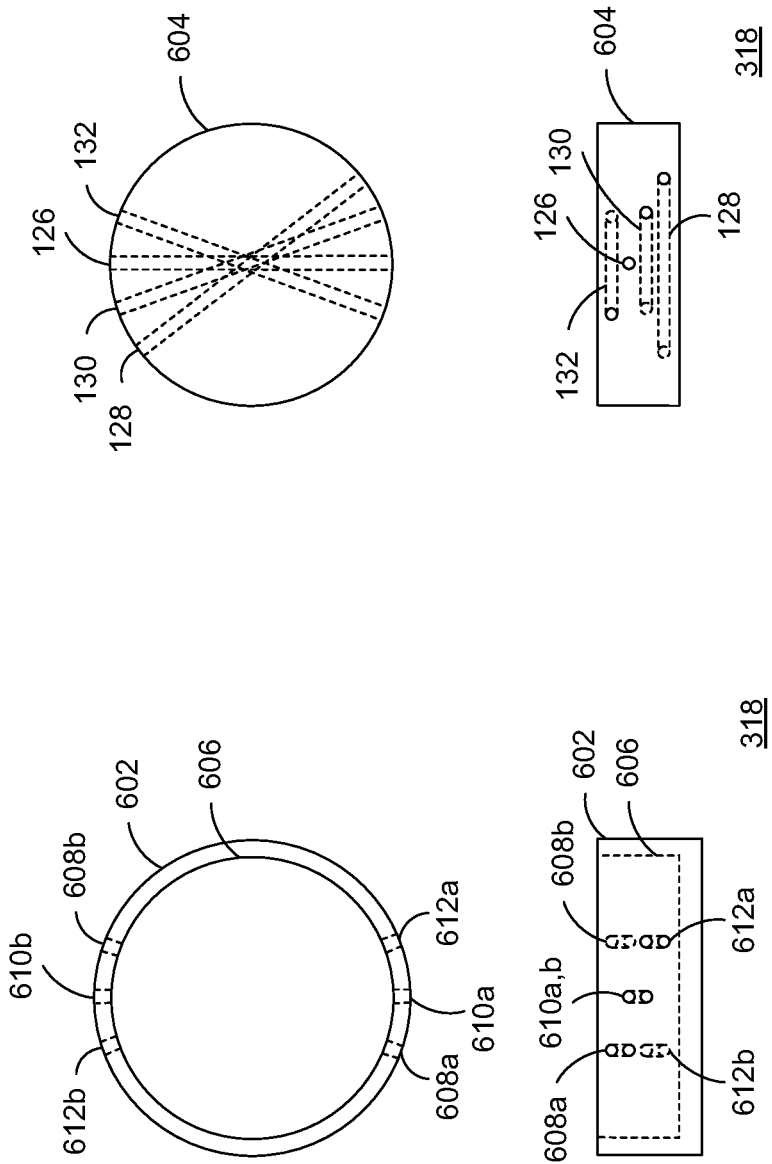
FIGS. 6A-6B illustrate top and side views of the exemplary rotary valve configuration of FIGS. 3A-3B.
Figure 7A:
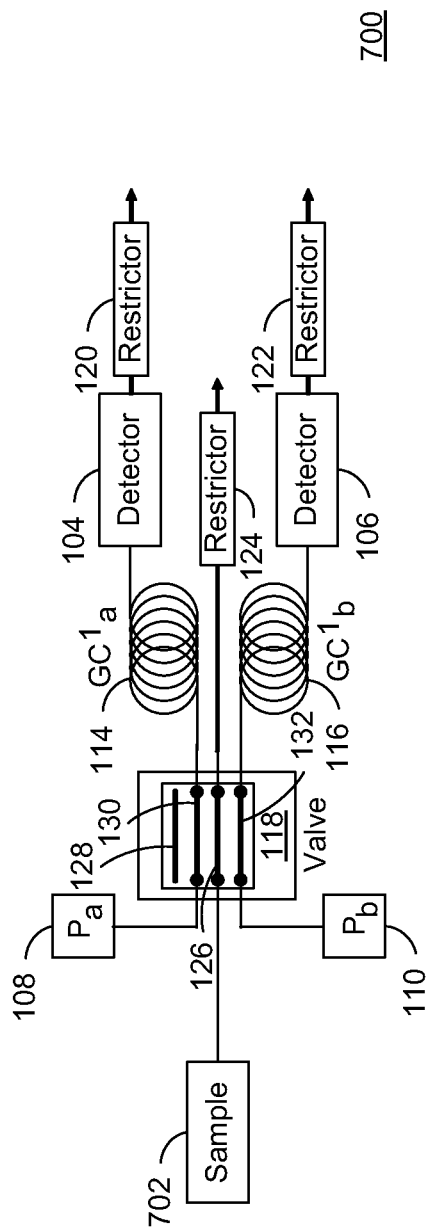
FIGS. 7A-7B illustrate a further exemplary sliding-plate valve configuration.
Figure 7B:
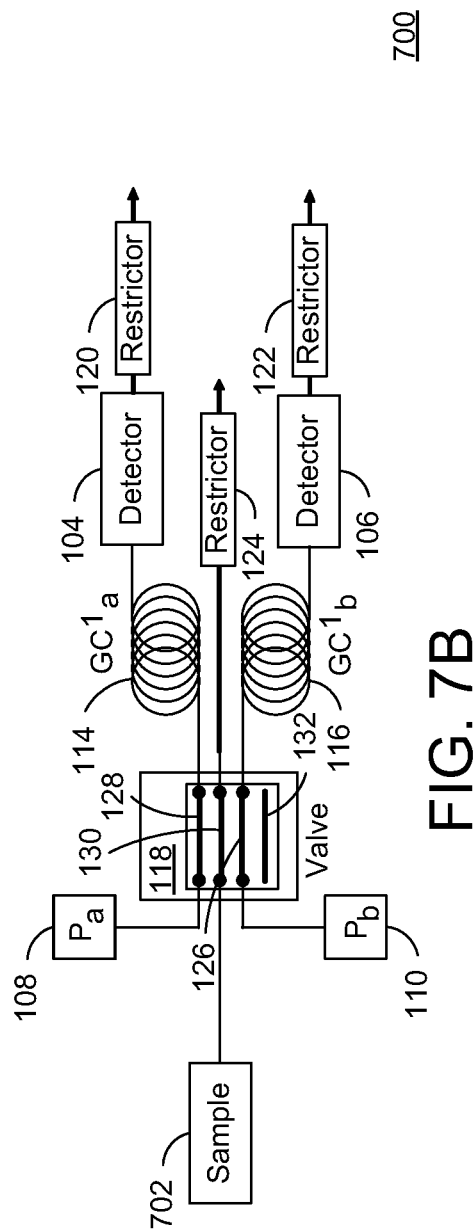

FIGS. 6A-6B show top and side views of the rotating valve 318. In FIGS. 6A-6B, the valve 318 includes circular valve body 602 with rotor opening 606 for a rotor 604, entry ports 608a-612a and exit ports 608b-612b of the circular valve body 602, and the sample paths 126-132 of the rotor 604. Advantageously, the entry ports 608a-612a and exit ports 608b-612b of the circular valve body 602, the sample paths 126-132 of the rotor 604, and the like, can be microfabricated structures. The rotating valve 318 also can be made with tubes corresponding to the sample paths 126-132 and that can be welded or soldered to a rotating plate serving as the rotor 604.

Advantageously, the physical distance employed for actuation with the valves 118 and 318 can be relatively small, and with no connecting flow paths (e.g., tubes or grooves 126-132 in the rotor 504 or the sliding-plate 404) that must pass over other entry or exit ports during actuation, before arriving to the final location.

Various advantages are provided by modulation scheme of the exemplary embodiments, for example, including (1) improved signal to noise ratio and injection band widths by virtue of the compression resulting from the high pressure second dimension columns; (2) increased modulation frequency by virtue of the valve design and dual second dimension columns; (3) flow isolation for all three columns and therefore independent flow optimization for all columns; (4) the capability of using different stationary phases on the two second dimension columns to enhance the selectivity of the separation; (5) improved capability for 100% sample transfer between the first and second dimensions, by virtue of the valve design and dual second dimension columns (which is usually not the case with valve modulators, for example, as described in United States Patent Application Publication No. 20020148353 A1 of Seeley); (6) the potential for integration with microfabricated components (e.g., such as valves, columns, and detectors); (7) the capability of achieving a faster and/or higher resolution GCXGC separation by taking advantage of the faster modulation frequency and sharp second dimension injections and therefore the ability to tolerate sharper first dimensional peaks; and (8) this valve modulator, unlike most previously known, does not generate dilution in the process of manipulating the flow.

Further embodiments are also possible. For example, a variety of other valve types can employed based on the teachings of the exemplary embodiments so as to provide similar flow configurations. In further exemplary embodiments, a single second dimension column can be used that is connected by a tee junction to both valve injection points. Similarly, both second dimension columns can be coated with the same stationary phase, if the additional selectivity of a third stationary phase is not necessary. More than two second dimension columns can also be employed, with a suitable valve design, and which would allow for even faster modulation frequencies. In addition, the modulation frequency can be further increased, without increasing valve actuation times or reducing second dimension separation times, by employing several valve modulators in parallel, each configured as in FIGS. 1-3, and with offset valve cycle periods, wherein the first dimension effluent can be split evenly to the input ports of each valve modulator. Although the system complexity may rapidly increase for microfabricated systems, such complexity should be easily accommodated.

In further exemplary embodiments, the exemplary sliding-plate valve configuration of FIGS. 1A-1B can be configured as injection system 700 and 800 for gas chromatographic measurements, as shown in FIGS. 7A-7B and 8A-8B, respectively. The systems 700 and 800 operate in a similar manner as that of FIGS. 1A-1B, except for the following differences. For example, the exemplary systems 700 and 800 can be used in one of several fashions, including employing only a single or several GC columns as the outlet(s). The valve 118 operation is similar to the operation as described with respect to FIGS. 1A-1B, except that no first-dimension GC columns 112 upstream of the injector 102 need be employed, as shown in FIGS. 7A-7B and 8A-8B.

In FIG. 7, the novel valve configuration includes a sample source 702 as an upstream component. As long as a gaseous sample is provided, the valve 118 can act to focus a plug for injection onto the respective chromatographic columns 114 and 116. The plug width that can be generated by the valve 118 is limited by the pressure differential between the sample source and the auxiliary pressure sources 108 ($P_a$) and 110 ($P_b$). This can result in plugs that are significantly narrower than conventional GC injection devices can provide. As noted above, the novel valve configuration or a similarly configured valve can be configured to service from one up to many GC columns in further exemplary embodiments. The columns can have differing chemistry, film thickness, temperature and pressure programs, cross-sectional area, length, and the like or have similar characteristics. FIG. 8 illustrates a further embodiment, where the sample 702 is a liquid sample. In this scenario, the sample is converted to a gas phase, for example, using a heated chamber and/or a mixing chamber ($V_s$) 804 (often referred to as a vaporization chamber or expansion chamber) that is inline between the sample source 702 and the valve 118.

All or a portion of the devices and subsystems of the exemplary embodiments can be conveniently implemented by the preparation of application-specific integrated circuits or devices and/or by interconnecting an appropriate network of conventional component circuits and/or devices, as will be appreciated by those skilled in the relevant art(s). Thus, the exemplary embodiments are not limited to any specific combination of hardware circuitry and/or devices.

Although the exemplary embodiments are described in terms of sliding-plate, and rotary valve configurations, the exemplary embodiments can be employed with any other suitable valve configurations, as will be appreciated by those skilled in the relevant art(s).

While the present inventions have been described in connection with a number of exemplary embodiments, and implementations, the present inventions are not so limited, but rather cover various modifications, and equivalent arrangements, which fall within the purview of the present claims.

What is claimed is:

1. An apparatus for two-dimensional gas chromatography, comprising:
a valve including first and second positions, and first, second, third, and fourth flow paths, wherein the valve, while in the first position, is configured to:
collect a first gas sample from a first dimension gas chromatography column via the first flow path;
provide a connection between a first pressure source and a first, second dimension gas chromatography column via the second flow path;
provide a connection between a second pressure source and a second, second dimension gas chromatography column via the third flow path; and
maintain the fourth flow path in a disconnected state; and
wherein the valve, while in the second position, is configured to:
introduce the first collected gas sample in the first flow path to the second, second dimension gas chromatography column via the first flow path, with aid of the second pressure source;
collect a second gas sample from the first dimension gas chromatography column via the second flow path;
provide a connection between the first pressure source and the first, second dimension gas chromatography column via the fourth flow path; and
maintain the third flow path in a disconnected state;
an injector coupled to an inlet of the first dimension gas chromatography column for injecting a gas to be analyzed into the first dimension gas chromatography column;
a first restrictor coupled to the valve for restricting the gas injected into the first dimension gas chromatography column by the injector to increase a compression ratio in the first dimension gas chromatography column;
a first detector coupled to an outlet of the first, second dimension gas chromatography column for performing gas chromatography detection in the first, second dimension gas chromatography column;
a second restrictor coupled to the first detector for restricting gas in the first, second dimension gas chromatography column to increase a compression ratio in the first, second dimension gas chromatography column;
a second detector coupled to an outlet of the second, second dimension gas chromatography column for performing gas chromatography detection in the second, second dimension gas chromatography column; and
a third restrictor coupled to the second detector for restricting gas in the second, second dimension gas chromatography column to increase a compression ratio in the second, second dimension gas chromatography column.

2. The apparatus of claim 1, wherein the first or the second detector comprises a thermal conductivity detector (TCD).

3. A method for comprehensive two-dimensional gas chromatography conducted with a valve having first and second positions, and first, second, third, and fourth flow paths, the method comprising the steps of:
putting the valve in the first position, and:
collecting a first gas sample from a first dimension gas chromatography column via the first flow path;
providing a connection between a first pressure source and a first, second dimension gas chromatography column via the second flow path;
providing a connection between a second pressure source and a second, second dimension gas chromatography column via the third flow path; and
maintaining the fourth flow path in a disconnected state;
putting the valve in the second position, and:
introducing the first collected gas sample in the first flow path to the second, second dimension gas chromatography column via the first flow path, with aid of the second pressure source;
collecting a second gas sample from the first dimension gas chromatography column via the second flow path;
providing a connection between the first pressure source and the first, second dimension gas chromatography column via the fourth flow path; and
maintaining the third flow path in a disconnected state.

4. The method of claim 3, wherein for comprehensive two-dimensional gas chromatography, setting a time to collect the first gas sample before moving the valve to the second position equal to or less than a volume of the first gas sample divided by a volumetric flow rate of an outlet of the first dimension gas chromatography column.

5. The method of claim 4, further comprising setting a time spent by the valve in the second position equal to the time to collect the first gas sample.

6. The method of claim 5, further comprising setting a separation time employed on both the first and second, second dimension gas chromatography columns to less than a total time spent in the first and second valve positions, and equal to twice a reciprocal of a modulation frequency.

7. The method of claim 3, further comprising injecting a gas to be analyzed into the first dimension gas chromatography column via an injector coupled to an inlet of the first dimension gas chromatography column.

8. The method of claim 7, further comprising restricting the gas injected into the first dimension gas chromatography column by the injector to increase a compression ratio in the first dimension gas chromatography column via a first restrictor coupled to the valve.

9. The method of claim 3, further comprising performing gas chromatography detection in the first, second dimension gas chromatography column via a first detector coupled to an outlet of the first, second dimension gas chromatography column.

10. The method of claim 9, further comprising restricting gas in the first, second dimension gas chromatography column to increase a compression ratio in the first, second dimension gas chromatography column via a second restrictor coupled to the first detector.

11. The method of claim 10, further comprising performing gas chromatography detection in the second, second dimension gas chromatography column via a second detector coupled to an outlet of the second, second dimension gas chromatography column.

12. The method of claim 11, further comprising restricting gas in the second, second dimension gas chromatography column to increase a compression ratio in the second, second dimension gas chromatography column via a third restrictor coupled to the second detector.

13. The method of claim 11, wherein the second detector comprises a thermal conductivity detector (TCD).

14. The method of claim 9, wherein the first detector comprises a thermal conductivity detector (TCD).

15. The method of claim 2, wherein the valve comprises a sliding-plate type valve.

16. The method of claim 3, wherein the valve comprises a rotary type valve.

17. A method for gas chromatography conducted with a valve having first and second positions, and first, second, third, and fourth flow paths, the method comprising the steps of:

putting the valve in the first position, and:

collecting a first sample from a sample source via the first flow path;

providing a connection between a first pressure source and a first gas chromatography column via the second flow path;

providing a connection between a second pressure source and a second gas chromatography column via the third flow path; and maintaining the fourth flow path in a disconnected state;

putting the valve in the second position; and:

introducing the first collected sample in the first flow path to the second gas chromatography column via the first flow path, with aid of the second pressure source;

collecting a second sample from the sample source via the second flow path;

providing a connection between the first pressure source and the first gas chromatography column via the fourth flow path; and maintaining the third flow path in a disconnected state.

18. The method of claim 17, wherein the first and second samples are in a gas phase.

19. The method of claim 17, wherein the first and second samples are in a liquid phase, and the method further comprises converting the first and second samples in the liquid phase to a gas phase via a chamber provided between the sample source and the valve.

* * * * *